US007001993B1

(12) United States Patent
Koide

(10) Patent No.: US 7,001,993 B1
(45) Date of Patent: Feb. 21, 2006

(54) HUMAN ANTITHROMBIN VARIANTS

(75) Inventor: Takehiko Koide, Hyogo-ken (JP)

(73) Assignee: Aventis Pharma Ltd., Tokyo (JP)

( * ) Notice: Subject to any disclaimer, the term of this patent is extended or adjusted under 35 U.S.C. 154(b) by 0 days.

(21) Appl. No.: 10/018,815

(22) PCT Filed: Jun. 22, 2000

(86) PCT No.: PCT/JP00/04101

§ 371 (c)(1),
(2), (4) Date: Jun. 6, 2002

(87) PCT Pub. No.: WO00/78811

PCT Pub. Date: Dec. 28, 2000

(30) Foreign Application Priority Data

Jun. 23, 1999 (JP) ............................... 11-176967

(51) Int. Cl.
*A61K 35/14* (2006.01)
*C07H 21/04* (2006.01)
*C07K 1/00* (2006.01)

(52) U.S. Cl. ..................... 530/393; 536/23.5; 530/350; 530/380; 930/250; 930/10

(58) Field of Classification Search ............... 435/69.2, 435/320.1, 463; 536/23.5; 530/350, 3.93, 530/380, 393; 930/250, 10
See application file for complete search history.

(56) References Cited

U.S. PATENT DOCUMENTS 5,420,252 A 5/1995 Kato et al.
5,618,713 A 4/1997 Zettlmeissl et al.

FOREIGN PATENT DOCUMENTS

| EP | 0 384 122 | 8/1990 |
|---|---|---|
| JP | 2-262598 | 10/1990 |
| JP | 5-339292 | 12/1993 |
| JP | 9-71600 | 3/1997 |
| WO | WO 91/00291 | 1/1991 |

OTHER PUBLICATIONS

Olds R. J. et al. Anthitrombin III Budapest: a single amino acid substitution (429Pro to Leu) in a region higly conserved in the serpin family, Blood 1992, 79, 1206-1212.*
Sorensen P. J. et al. Distiction of two patologic antitrombin III molecules: antithrombin III"Aalborg" and antithrombin III "Budapest", Thromb. Res. 1982, 26, 211-219.*

Fan, B., et al., "Lysine-Heparin Interactions in Antithrombin. Properties of K125M and K290M, K294M, K297M Variants," *Biochemistry*, 33:14156-14161 (1994).
Fitton, H. L., et al., "Five Antithrombin Variants, Four Associated with Thrombosis," *Blood Coagulation and Fibrinolysis*, 8:145-148 (1997).
Huntington et al.; "Mechansim of Heparin Activation of Antithrombin. Evidence for Reactive Center Loop Preinsertion With Expulsion Upon Heparin Binding"; Biochemistry, vol. 35, pp. 8495-8503, (1996).
Huntington et al.; "Conformational Conversion of Antithrombin to a Fully Activated Substrate of Factor Xa Without Need for Heparin"; Biochemistry, vol. 37, pp. 3272-3277, (1998).
Meagher et al.; "Deconvolution of the Fluorescence Emission Spectrum of Human Antithrombin and Identification of the Tryptophan Residues That are Responsive to Heparin Binding"; The Journal of Biological Chemistry, vol. 273, No. 36, pp. 23283-23289, (1998).
Shirk et al.; "Role of the H Helix in Heparin Binding to Protein C Inhibitor" ; The Journal of Biological Chemistry; vol. 269, No. 46, pp. 28690-28695, (1994).
Futamura et al.; "Serine 380 (P14)→Glutamate Mutation Activates Antithrombin as an Inhibitor of Factor Xa"; The Journal of Biological Chemistry, vol. 275, No. 6, pp. 4092-4098, (2000).
F. Tokunaga et al., Amino Acid Sequence of Porcine Antithrombin III, *J Biochem*, 116,1164-70 (1994).
Chandra et al., Isolation and sequence characterization of a cDNA clone of human antithrombin III, *Proc Natl Acad Sci, USA* 80, 1845-1848 (1983).
Koide, T., Isolation and Characterization of Antithrombin III from Human, Porcine, and Rabbit Plasma, and Rat Serum, *J. Biochem* 86, 1841-1850 (1979).

* cited by examiner

*Primary Examiner*—Rebecca E. Prouty
*Assistant Examiner*—Malgorzata A. Walicka
(74) *Attorney, Agent, or Firm*—Finnegan, Henderson, Farabow, Garrett, & Dunner, L.L.P.

(57) ABSTRACT

Human antithrombin variants showing a high protease inhibitory activity even in the absence of heparin wherein at least one of the amino acids at positions 78, 278, 378 and 380 in the amino acid sequence of natural human antithrombin is substituted by another amino acid. Preferable examples thereof are human antithrombin variants wherein the amino acid at position 78 is substituted by Phe; the amino acid at position 278 is substituted by Ala, Arg, Asn, Gly, His, Tyr or Val; the amino acid at position 378 is substituted by Lys, Asn or Val; and/or the amino acid at position 380 is substituted by Ala, Asp, Gly, His, Ile, Leu, Asn, Pro, Arg, Thr, Tyr or Val.

8 Claims, 1 Drawing Sheet

US 7,001,993 B1

HUMAN ANTITHROMBIN VARIANTS

TECHNICAL FIELD TO WHICH THE INVENTION BELONGS

This invention relates to an artificial human antithrombin variant that has a high protease inhibitory activity in the absence of heparin. More particularly, the invention relates to a human antithrombin variant having a three dimensional structure after binding to heparin, wherein the three dimensional structure of natural human antithrombin molecule is modified by a genetic engineering procedure. The variant of the invention can be used for the treatment of, for example, DIC, thrombotic diseases or gestosis.

PRIOR ART

It has been disclosed that there are various kinds of antithrombin activities in natural antithrombin, and antithrombins I to VI have been proposed. However, in view of the fact that only antithrombin III has been isolated as protein up to the present time, antithrombin III is now referred to simply as antithrombin. Accordingly, the antithrombin III is hereinafter referred to as antithrombin in regard to this invention.

Natural human antithrombin is a single-strand glycoprotein having a molecular weight of 58,000, which has an inhibitory activity on proteases in the blood coagulation system. Natural human antithrombin is biosynthesized as a precursor protein consisting of 464 amino acid residues, but a signal peptide consisting of 32 residues is cleaved out in the course of secretion. Thus, mature human antithrombin circulating in blood vessels is composed of 432 amino acid residues. All of six cysteine residues (Cys) form disulfide bonds, and human antithrombin molecule is stabilized with the S—S bridges at three sites of Cys8–Cys128, Cys21–Cys95 and Cys247–Cys430. Natural human antithrombin contains approximately 15% of sugars, and complex-type sugar chains are attached to asparagine residues at four positions (Asn96, Asn135, Asn155 and Asn192). The molecular site of natural human antithrombin which interacts directly with and binds to the active center of protease is referred to as a reactive site, which is Arg393-Ser394 located near the C-terminus of peptide chain.

Natural human antithrombin is a plasma protein belonging to a serpin superfamily like $\alpha_1$-antitrypsin and heparin cofactor II, and is a main control factor in the blood coagulation system which controls activities of main coagulating enzymes, such as thrombin, activated factor X (factor Xa), activated factor IX (factor IXa), etc. Natural human antithrombin having such pharmacological activities has been used for the normalization of abnormally accelerated coagulation, more specifically, disseminated intravascular coagulation (DIC), and gestosis whose main symptoms are hypertension, proteinuria and edema during the period of pregnancy, as well as for treating hyper-thrombopoiesis derived from congenital human antithrombin deficiency.

It is well known that natural human antithrombin has a high affinity for heparin and that inhibition rates on thrombin and factor Xa can be accelerated to 1000 times and 300 times, respectively, in the presence of heparin.

Analyses of primary structure level so far made have revealed that a heparin-binding site is located in the N-terminal region of natural human antithrombin and the reactive site with protease is located near the C-terminus (Arg393-Ser394). Moreover, 5–10% of natural human antithrombin in blood is a molecular species wherein a sugar chain is not bound to Asn135 (human antithrombin β), and this species reveals a higher heparin affinity than a dominant molecular species (human antithrombin α) does.

Natural human antithrombin molecule is, like other blood serpins, a protein which comprises, in a three-dimensional structure, several strands (hereinafter abbreviated as s1A-s4C) composed of antiparallel β sheets, roughly classified to three directions of A, B and C, nine α-helixes (hereinafter abbreviated as hA-hI) and a coil structure moiety (Stein P E, Carrell R W, Nature Struct Biol 2: 96, 1995). Recently, reports on X-ray crystal structure at 2.6 Å of the antithrombin dimers of native form and latent form (Skinner R., et al., J. Mol. Biol. 266: 601, 1997) and on crystal structures at 2.9 Å of a complex with pentasaccharide of the core moiety of a high-affinity heparin (Jin L., et al., Proc. Natl. Acad. Sci. USA, Vol. 94: 14683, 1997) have revealed a three-dimensional interacting site of natural human antithrombin with heparin and dynamic structural change in antithrombin molecule caused by heparin binding.

On the basis of these dynamic structural changes in natural human antithrombin molecule, the present inventor has thought that human antithrombin is an "incomplete" serpin as an inhibitor in the absence of heparin and would become a "complete" inhibitor only in the presence of heparin.

On the basis of these prior findings, preparation of a human antithrombin variant having a high protease-inhibitory activity even in the absence of heparin has been attempted by exchanging amino acid(s) at the specific position(s) in natural human antithrombin. For example, a human antithrombin variant is disclosed wherein one, two or more of the amino acids at positions 49, 96, 135, 155, 192, 393 and 394 in natural human antithrombin are replaced with other amino acids (Japanese Patent Kokai No. 262598/1990). Also, another human antithrombin variant is disclosed wherein at least one of the amino acids in four regions of positions 11–14, 41–47, 125–133 and 384–398 is replaced with other amino acids, alone or in combination in the respective regions (Japanese Patent Kokai No. 339292/1993). Since these variants do not always exert a satisfactory effect, there has been a demand for the preparation of a human antithrombin variant having a still more potent protease-inhibitory activity in the absence of heparin.

DISCLOSURE OF THE INVENTION

Purpose of the present invention is to provide a novel human antithrombin variant, which can act as a complete inhibitor in the absence of heparin and exert a high protease-inhibitory activity.

When natural human antithrombin acts as a protease inhibitor, a great conformational change occurs in the reactive loop of human antithrombin. More specifically, the reactive loop protruding from the molecule surface of natural human antithrombin is recognized as a "substrate" for target protease, and the peptide bond at the reactive site [P1 (Arg393)-P1' (Ser394)] is cleaved with the protease. At this time, an acyl bond is formed between the carbon of the carbonyl group of Arg393 at P1 and the oxygen of the hydroxyl group of the active center Ser195 of the protease, whereby an acyl-enzyme complex is formed and, simultaneously, 15 residues (P1–P15) on the N-terminus of the cleaved reactive loop are incorporated between s3A and s5A to form a new strand (s4A). At this point, Arg393 moves approximately 70 Å from one end to another in human antithrombin molecule, together with the protease. This dynamic change is thought to be significant to form a stable complex with a protease. There has also been found a latent form of natural human antithrombin or plasminogen activator inhibitor 1 wherein the reactive site, though not cleaved, is inserted into the molecule as s4A. From these facts, a stable structure of serpin is thought to reside in the formation of s4A.

Since the reactive loop of natural α-antitrypsin is completely exposed over the molecule surface and the side chain of Met358 at P1 is oriented outwardly from the molecule to form complementary conformation to the active site of serine protease, reactivity with protease is high and intramolecular insertion of the reactive loop after cleavage is apt to occur. However, since the side chain of Arg393 at P1 of natural human antithrombin is oriented inwardly in the molecule, reactivity with protease is extremely low (Jin L., et al., Proc. Natl. Acad. Sci. USA, 94: 14683, 1997). The present inventor's attention has been drawn to a still more significant fact that the reactive loop in natural human antithrombin is incorporated into strands at P14 (Ser380) and P15 (Gly379), which provides strands with distortion and also makes insertion of the cleaved loop difficult. Binding of heparin to natural human antithrombin induces conformational changes at various sites of human antithrombin molecule, and the amino acids at P14 (Ser380) and P15 (Gly379) could be extruded from the strand by an allosteric effect (steric hindrance effect) of heparin binding and dislocated to the same location as in α-antitrypsin (Jin L., et al., Proc. Natl. Acad. Sci. USA, 94: 14683, 1997).

The present inventor has analyzed and studied conformational change in the respective reactive loops of the above human antithrombin, plasminogen activator inhibitor 1 and $\alpha_1$-antitrypsin, and, as a result, have judged that P14 (Ser380) in natural human antithrombin is a key site for constructing a suitable three dimensional structure acting as a complete inhibitor in the absence of heparin and having a high protease-inhibitory activity. Moreover, in view of that the site of P15-P10 in the reactive loop of natural human antithrombin is referred to as "proximal hinge" region, the present inventor has studied its three dimensional structural feature in human antithrombin and have found that this proximal hinge region plays a role as a hinge when the reactive loop is incorporated as s4A. Based on the finding, the present inventor has judged that the site at P16 (Glu378) corresponding to the base of said hinge is also a site to be replaced by another suitable amino acid for the preparation of human antithrombin variant having a proper three dimensional structure and a high protease-inhibitory activity, together with the site at P14.

On the other hand, it is known that the reactive loop in natural human antithrombin is inserted into the molecule as s4A between s3A and s5A when cleaved with a protease and that the region participating in opening these strands is the shutter region wherein hB (Ser79-Thr90) is centered (Stein P E, Carrel R W, Nature Struct Biol 2: 96, 1995). The present inventor has found that, on opening between s3A and s5A, the hydrogen bonds between both strands are first cleaved and then these strands slide over the groove of hB, and that "easier opening" of this region relates to "easier inserting" of the reactive loops. In summary, the shutter region in natural human antithrombin is an important region which influences upon the opening and closing between s3A and s5A and further influences upon binding of heparin and activity of antithrombin. Then, the present inventor has judged that a human antithrombin variant having a three dimensional structure with a high protease-inhibitory activity can be produced by replacing the amino acid at position 78 (Leu78), which corresponds to the base of the shutter region, with another amino acid.

Then, the present inventor has analyzed and studied dynamic structural changes in natural human antithrombin and promotion of protease-inhibitory activity, which are induced by heparin binding; in particular, the three dimensional structure of each amino acid in the heparin binding region. It has been hitherto elucidated that the heparin binding region in natural human antithrombin consists of a group of basic amino acid residues which are located at hA and hD, based on analysis of anomalous cases such as antithrombin TOYAMA wherein Arg at position 47 is replaced with Cys (Koide T., Takahashi K., et al., Proc. Natl. Acad. Sci. USA, 81: 289, 1984) or chemical modification experiments, as well as analysis of variants prepared by site-specific mutagenesis. The above-mentioned X-ray analysis of crystal structure (Jin L., et al., Proc. Natl. Acad. Sci. USA, 94: 14683, 1997) has elucidated that the heparin-derived pentasaccharide binding sites in natural human antithrombin are in hD (side chains of Lys125 and Arg129), hA (side chains of Arg46 and Arg47, and main chain amide of Asn45), the N-terminal region (side chains and main chain amides of Lys11 and Arg13), and main chain amide of Glu113 and side chain and main chain amides of Lys114 in the "P-helix" (P is originated from pentasaccharide), which is formed between hC-hD through binding with pentasaccharide. When pentasaccharide comes into contact, Arg46 and Arg47 move by 17 Å and 8 Å, respectively, to form a hydrogen bond with the sulfate group of the sugar chain. Moreover, hD is inclined by an angle of about 10 degrees toward the direction of pushing s2A and s3A, and the coil structure of Glu113-Gln118 on its N-terminal side is modified to two-twisted hP toward the right-angled direction to hD. Moreover, a one and half-twisted helix is also formed on the C-terminal side of hD, in such ways that side chains of Arg132, Lys133 and Lys136 are directed toward the pentasaccharide binding site. These residues are far apart from the pentsaccharides and thus a hydrogen bond is not formed between them, but it is highly possible for these residues to interact with a long-chain heparin. Moreover, in the said-native form of human antithrombin, the amino acid residues at P14 and P15 in the hindered reactive loop is extruded by an allosteric effect caused by elongation of hD, and distortion of strands is eliminated and simultaneously the side chain of Arg393 at P1 is directed outwardly from the molecule, which transforms into a form which may react as an inhibitor (Pike R N, et al., J. Biol. Chem. 272: 19652, 1997). Moreover, the N-terminal region of human antithrombin (Ile22-Arg46) moves greatly when bound with pentasaccharide and thus plays a role as a steric gate for stabilizing an antithrombin-pentasaccharide complex (Fittom H L., et al., Protein Science 7: 782, 1998). In comparing three dimensional structures of the native form and latent form of natural human antithrombin, hD of the native form is slightly twisted, heparin binding site, Arg47, Lys125 and Arg129, are directed toward the pentasaccharide-binding region, and the NE group of Arg129 forms a hydrogen bond with the side chain of Asp278 to stabilize the said side chain, which facilitates ionic interaction with the sulfate groups of pentasaccharide. However, in the latent form, hD elongates straightforward, Arg47 and Lys125 form hydrogen bonds with Ser112 and Ile7, respectively, and all amino acid residue regions, which are significant for heparin binding, are not directed toward heparin binding regions (Skinner R., et al., J. Mol. Biol. 266: 601, 1997). In view of this, the present inventor has judged that the three dimensional structure may be altered, even in the absence of heparin, to a conformation similar to that in the presence of heparin, by prior cleavage of a hydrogen bond between Arg129 and Asp278. Based on the judgement, the present inventor thought that replacing the amino acid at position 278 (Asp278), which binds to Arg129 via a hydrogen bond, with another amino acid can produce an antithrombin variant having a suitable three dimensional structure with a high protease-inhibitory activity.

As depicted above, the present inventor has studied information on dynamic conformational change of antithrombin resulting from binding of heparin to natural human antithrombin as previously analyzed and, as a result, have found out a preferred site to be modified or altered in the three dimensional structure for promoting protease-inhibitory activity of natural human antithrombin. More specifically, the present inventor has reached the conclusion that replacement with one, two or more of other amino acids in the hinge region of the reactive loop of natural human antithrombin, the hinge region to form s4A, as well as those sites involved in heparin binding can produce a human antithrombin variant having a suitable three dimensional structure with a high protease-inhibitory activity. The present inventor has made the earnest studies on improvement of human antithrombin variant based on the above-mentioned conclusion, and finally succeeded in preparing a novel human antithrombin variant having an appropriate three dimensional structure for a high protease-inhibitory activity, upon which this invention has been completed.

The present invention is directed to a human antithrombin variant, that is, a human antithrombin variant wherein at least one of amino acids at positions 78, 278, 378 and 380 in the amino acid sequence of natural human antithrombin is replaced with another amino acid. Of these human antithrombin variants, the following variants are particularly preferred:

a human antithrombin variant wherein the amino acid at position 78 in the amino acid sequence of natural human antithrombin is replaced with Phe, a human antithrombin variant wherein the amino acid at position 278 in the amino acid sequence of natural human antithrombin is replaced with the amino acid selected from Ala, Arg, Asn, Gly, His, Tyr and Val, a human antithrombin variant wherein the amino acid at position 378 in the amino acid sequence of natural human antithrombin is replaced with the amino acid selected from Lys, Asn and Val, and a human antithrombin variant wherein the amino acid at position 380 in the amino acid sequence of natural human antithrombin is replaced with the amino acid selected from Ala, Asp, Gly, His, Ile, Leu, Asn, Pro, Arg, Thr, Tyr and Val.

Moreover, the invention is directed to a DNA encoding the said human antithrombin variant.

DETAILED DESCRIPTION OF PREFERRED EMBODIMENTS

Figure 1:
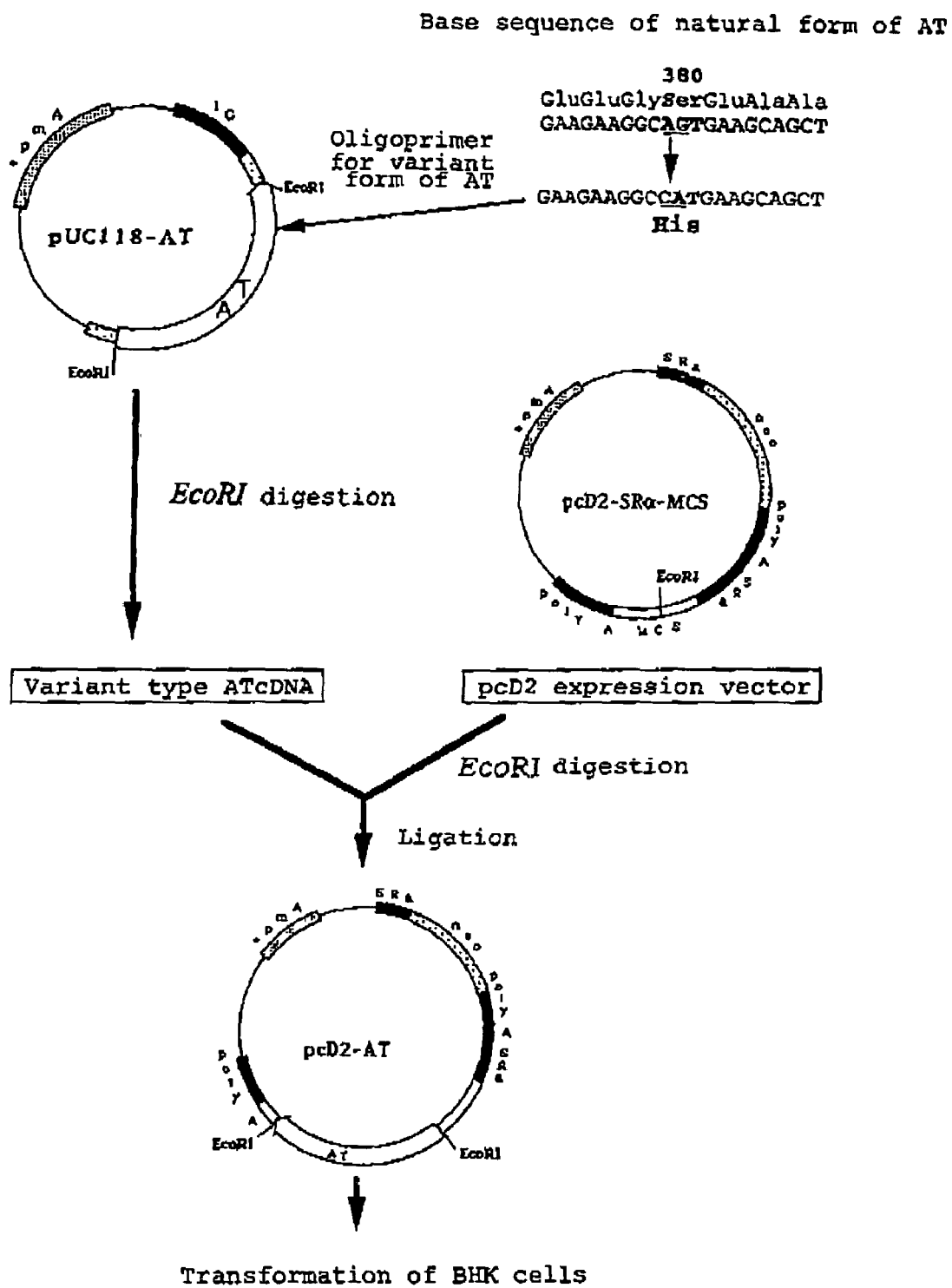
FIG. 1 shows construction of an expression vector for an antithrombin (AT) recombinant variant (in case of Ser380His).

The novel antithrombin variant of the invention was prepared by site-specific mutagenesis as a variant having a three dimensional structure, which is similar to that after binding with heparin. Namely, a cDNA coding the antithrombin variant was prepared by (1) preparation of a single-strand pUC118-AT, (2) introduction of mutation with Sculptor method, (3) confirmation of mutation insertion, and (4) EcoRI digestion. The variant cDNA was inserted into EcoRI-digested pcD2 expression vector. The resultant plasmid was used for transfection of BHK cells. The transfected BHK cells were selectively cultivated to produce the antithrombin variant (FIG. 1).

The invention is more specifically illustrated by way of the specific method for the preparation of a variant as set forth hereinafter.

To 2.5 µg (10 µl) of cDNA (single-stranded) for the native form of antithrombin was annealed 30 µl of a variant primer (0.475 OD/ml) for amino acid substitution to synthesize a full-length cDNA with DNA polymerase. Then, the nucleotide sequence was determined to confirm a formation of variant. cDNA (1.4 kb) for each antithrombin variant was integrated into EcoRI site of pcD2 vector and then cleaved with EcoRI and PstI to confirm the direction of the inserted sequence. The vector with sequence integrated in right direction was transfected into BHK cells for a large-scale production by a calcium phosphate method (FIG. 1). The neomycin-resistant, stably expressing cells were selected with G418 and pooled. The pooled stably expressing BHK (baby hamster kidney) cells were used to conduct pulse-chase experiment. $5 \times 10^5$ cells were seeded onto a 35 mm dish in diameter and cultured overnight. They were labeled with 6.8 µl of EXRE35S35S (100 µCi/ml) for 30 minutes. Then the cultured broth was exchanged with DME/10% FCS, Met, Cys, and then chase was performed for 8 hours to obtain culture media (CM) and cell extracts (CE) after 0, 0.5, 1, 2, 4 and 8 hours. The CM and CE at each point were immune-precipitated with an antibody and Staphylosorb™, then 8% SDS-PAGE (+SH) was performed, and the radioactivity in the resulting RI bands was measured to determine the secreted amounts of the recombinant antithrombin variant.

For the cell secreting a high amount of the antithrombin variant, the CM was collected after 8 hours chase. To 500 µl of the collected liquid was added thrombin or factor Xa, and, after reacting at 37° C. for 5 minutes or 60 minutes without heparin, or for 5 minutes with heparin, an immune precipitation was performed and an amount of the complex was determined by 10% SDS-PAGE (+SH).

1) Secretion

Secretion from BHK cells of each recombinant antithrombin variant is summarized in Table 1, which shows intracellular and secreted amounts after 8 hours chase, taking the radioactivity in pulse-labeling as 100%. A secreted amount of the native-type recombinant antithrombin was 89%, whereas Leu78Phe variant wherein Leu at position 78 was replaced with Phe showed a secretion amount of 90%. The variant wherein Asp at position 278 was replaced with Ala, Gly, His or Tyr (Asp278Ala, Asp278Gly, Asp278His or Asp278Tyr) showed a secretion of 104%, 104%, 165% or 160%, respectively, which were higher than that of the native-type recombinant antithrombin.

On the other hand, the variant wherein Asp at position 278 was replaced with Arg, Asn or Val (Asp278Arg, Asp278Asn or Asp278Val) showed secretion of 57%, 48% or 51%, respectively. A satisfactory secretion was given in all variants wherein Ser at position 380 was replaced with Ala, Arg, Asn, Asp, Gly, His, Pro, Thr, Tyr or Val (Ser380Ala, Ser380Arg, Ser380Asn, Ser380Asp, Ser380Gly, Ser380His, Ser380Pro, Ser380Thr, Ser380Tyr or Ser380Val). Especially, the variants replaced with Asn and Val provided a high secretion of 154% and 144%, respectively.

2) Complex-Forming Ability with Thrombin (TAT)

The results of studies on thrombin-antithrombin complex (TAT)-forming ability of each recombinant antithrombin variant are summarized in Table 2. Immediate TAT-forming ability in the absence of heparin, which is the greatest effect of the invention, was 131% for the Leu78Phe variant wherein Leu at position 78 was replaced with Phe, 163% for the Asp278His variant wherein Asp at position 278 was replaced with His, and 171% and 172% for the Ser380Gly and Ser380Tyr variants wherein Ser at position 380 was replaced with Gly and Tyr, respectively, in terms of the relative value when TAT-forming ability of a native type of recombinant is defined as 100%, and variants having a higher efficacy than that of a native type of recombinant were provided in every case. Moreover as shown in Table 2, in the interaction with thrombin over a prolonged period of time (120 minutes), Leu78Phe, Asp278His and Ser380Ala variants had the same level of a stable TAT-forming ability as the native type of recombinant antithrombin, and Asp278Ala, Asp278Val, Asp278Tyr, Ser380Gly and Ser380Tyr variants had a higher level of a stable TAT-forming ability than the native type of recombinant antithrombin.

Moreover, all variants could retain the immediate TAT-forming ability in the presence of heparin and have also been demonstrated as an effective antithrombotic agent to be used in combination with heparin.

3) Complex-Forming Ability with Factor Xa (Xa-AT)

The results of studies on factor Xa-antithrombin complex (Xa-AT)-forming ability of each recombinant antithrombin variant with factor Xa (Xa-AT) are summarized in Table 3. Immediate Xa-AT-forming ability in the absence of heparin, which is the greatest effect of this invention, was 106% for the Leu78Phe variant wherein Leu at position 78 was replaced with Phe, in terms of the relative value when Xa-AT-forming ability of a native-type of recombinant is defined as 100%. Also, values of 144%, 171% and 131% were obtained in the cases of Asp278Gly, Asp278His and Asp278Tyr variants wherein Asp at position 278 was replaced with Gly, His, or Tyr, respectively, and there could be obtained those variants having a higher efficacy than a native-type of recombinant antithrombin in every case. Moreover, in the interaction with factor Xa over a prolonged period of time (60 minutes), Leu78Phe, Asp278Gly, Asp278His and Ser380Tyr variants had the same level of a stable TAT-forming ability as the native-type of recombinant, and Asp278Val, Asp278Tyr and Ser380Gly variants had a higher level of a stable TAT-forming ability than the native-type of recombinant antithrombin.

Moreover, the immediate Xa-AT-forming ability in the presence of heparin in the cases of Leu78Phe, Asp278Ala and Asp278Gly variants was decreased approximately by half, as compared with native-type of recombinant antithrombin, and this has demonstrated effectiveness of these variants as a non-heparin-dependent inhibitor for factor Xa with a high efficacy. On the other hand, the Asp278Val, Asp278Tyr, Ser380Gly, Ser380Thr and Ser380Tyr variants have retained the immediate TAT-forming ability in the presence of heparin, thereby demonstrating their effectiveness as an antithrombotic agent to be used in combination with heparin.

TABLE 1

Secretion of AT Recombinant Variant Intracellular and secreted amounts after 8 hours chase, taking the radioactivity in pulse-labeling as 100%

| Recombinant | Intracellular amount (%) | Secreted amount (%) | Total |
| --- | --- | --- | --- |
| Native | 1.4 | 89 | 90.4 |
| Leu78Phe | 10 | 90 | 100 |
| Asp278Ala | 16 | 104 | 120 |
| AsP278Arg | 4.6 | 57 | 61.6 |
| Asp278Asn | 4.9 | 48 | 52.9 |
| AsP278Gly | 22 | 104 | 126 |
| AsP278His | 9.2 | 165 | 174.2 |
| Asp278Tyr | 16 | 160 | 176 |
| AsP278Val | 4.6 | 51 | 55.6 |
| Glu378Lys | 15 | 62 | 77 |
| Ser380Ala | 4.9 | 79 | 83.9 |
| Ser380Arg | 10 | 73 | 83 |
| Ser380Asn | 38 | 154 | 192 |
| Ser380Asp | 10 | 83 | 93 |
| Ser380Gly | 6.1 | 128 | 134.1 |
| Ser380His | 8.3 | 120 | 128.3 |
| Ser380Pro | 30 | 63 | 93 |
| Ser380Thr | 13 | 122 | 135 |
| Ser380Tyr | 11 | 78 | 89 |
| Ser380Val | 17 | 144 | 161 |

TABLE 2

TAT-Complex Forming by AT Recombinant Variant

| Recombinant AT | TAT (%) (−) heparin, 5 min. | TAT (%) (−) heparin, 120 min. | TAT (%) (+) heparin, 5 min. |
| --- | --- | --- | --- |
| Native | 100 | 100 | 100 |
| Leu78Phe | 131 | 93 | 81 |
| Asp278Ala | 102 | 108 | 99 |
| Asp278His | 163 | 95 | 89 |
| Asp278Val | 90 | 108 | 104 |
| Asp278Tyr | 105 | 106 | 104 |
| Ser380Ala | 56 | 86 | 118 |
| Ser380Gly | 171 | 112 | 98 |
| Ser380Tyr | 172 | 122 | 111 |

Value expressed in terms of the relative value when TAT-forming ability of native-type of recombinant AT is defined as 100%.

TABLE 3

Xa-AT-Complex Forming by AT Recombinant Variant

| Recombinant AT | Xa-AT (%) (−) heparin, 5 min. | Xa-AT (%) (−) heparin, 120 min. | Xa-AT (%) (+) heparin, 5 min. |
| --- | --- | --- | --- |
| Native | 100 | 100 | 100 |
| Leu78Phe | 106 | 88 | 53 |
| Asp278Ala | 80 | 56 | 44 |
| Asp278Gly | 144 | 87 | 54 |
| Asp278His | 171 | 80 | 89 |
| Asp278Val | 89 | 116 | 136 |
| Asp278Tyr | 131 | 156 | 161 |
| Ser380Gly | 56 | 114 | 168 |
| Ser380Thr | 8.8 | 52 | 128 |
| Ser380Tyr | 86 | 90 | 105 |

Value expressed in terms of the relative value when Xa-AT-forming ability of native-type of recombinant AT is defined as 100%.

INDUSTRIAL UTILITY OF THE INVENTION

According to the present invention, there can be provided a novel human antithrombin variant, which has an appropriate three dimensional structure capable of exhibiting a high protease-inhibitory activity even if heparin is not present. The recombinant human antithrombin variant of the invention is useful as a therapeutic agent of, for example, thrombotic diseases or gestosis.

The invention claimed is:

1. A human antithrombin variant wherein the amino acid at position 78 in the amino acid sequence of natural human antithrombin is replaced with Phe.

2. A human antithrombin variant wherein the amino acid at position 278 in the amino acid sequence of natural human antithrombin is replaced with the amino acid selected from Ala, Arg, Asn, Gly, His, Tyr, and Val.

3. A human antithrombin variant wherein the amino acid at position 378 in the amino acid sequence of natural human antithrombin is replaced with the amino acid selected from Lys, Asn, and Val.

4. A human antithrombin variant wherein the amino acid at position 380 in the amino acid sequence of natural human antithrombin is replaced with the amino acid selected from Ala, Asp, Gly, His, Asn, Pro, Thr, and Arg.

5. A DNA encoding the human antithrombin variant as claimed in claim 1.

6. A DNA encoding the human antithrombin variant as claimed in claim 2.

7. A DNA encoding the human antithrombin variant as claimed in claim 3.

8. A DNA encoding the human antithrombin variant as claimed in claim 4.

* * * * *